(12) United States Patent
Villamil Torres et al.

(10) Patent No.: US 10,231,974 B2
(45) Date of Patent: Mar. 19, 2019

(54) PHARMACEUTICAL COMPOSITION EFFECTIVE IN PREVENTING THE ADVERSE EFFECTS ASSOCIATED WITH THE PROLONGED USE OF DIHYDROFOLATE REDUCTASE INHIBITORS

(71) Applicant: Companion Supplements, LLC, Sunrise, FL (US)

(72) Inventors: Julio César Villamil Torres, Bogota (CO); Camilo Rey Ferro, Sunrise, FL (US)

(73) Assignee: Companion Therapeutics, LLC, Sunrise, FL (US)

( * ) Notice: Subject to any disclaimer, the term of this patent is extended or adjusted under 35 U.S.C. 154(b) by 323 days.

(21) Appl. No.: 15/146,874

(22) Filed: May 4, 2016

(65) Prior Publication Data
US 2017/0319586 A1    Nov. 9, 2017

(51) Int. Cl.
| | | |
|---|---|---|
| *A61K 36/00* | (2006.01) | |
| *A61K 31/519* | (2006.01) | |
| *A61K 9/00* | (2006.01) | |
| *A61K 9/48* | (2006.01) | |
| *A61K 31/198* | (2006.01) | |
| *A61K 31/525* | (2006.01) | |
| *A61K 31/675* | (2006.01) | |
| *A61K 31/714* | (2006.01) | |
| *A61K 36/28* | (2006.01) | |

(52) U.S. Cl.
CPC .......... *A61K 31/519* (2013.01); *A61K 9/0053* (2013.01); *A61K 9/4825* (2013.01); *A61K 9/4833* (2013.01); *A61K 31/198* (2013.01); *A61K 31/525* (2013.01); *A61K 31/675* (2013.01); *A61K 31/714* (2013.01); *A61K 36/28* (2013.01)

(58) Field of Classification Search
CPC ..................................................... A61K 36/00
See application file for complete search history.

(56) References Cited

U.S. PATENT DOCUMENTS

| | | |
|---|---|---|
| 6,426,424 B1 | 7/2002 | Ashmead et al. |
| 7,947,662 B2 | 5/2011 | Valoti et al. |
| 8,642,581 B1 | 2/2014 | Halevie-Goldman |
| 2002/0037899 A1 | 3/2002 | Baggott et al. |
| 2004/0197430 A1 | 10/2004 | Meyrowitz |
| 2011/0081329 A1 | 4/2011 | Smith et al. |
| 2014/0073598 A1 | 3/2014 | Daniels et al. |

FOREIGN PATENT DOCUMENTS

WO    2007013987 A2    2/2007

OTHER PUBLICATIONS

PC Liver Detox, Oct. 1, 2012.
Liska, Deann J, The Role of Detoxification in the Prevention of Chronic Degenerative Diseases, ANSR—Applied Nutritional Scince Reports (Aug. 2002).
http://www.synergisticseurope.com/detox-with-d-toxol#dtoxoladultdosage. (2016).
Czarnecka-Operacz, M. et al., The possibilities and principles of methotrexate treatment of psoriasis—the updated knowledge. Advances in Dermatology and Allergology/Postepy Dematologil, 31(6):392-400 (2014).

*Primary Examiner* — Qiuwen Mi
(74) *Attorney, Agent, or Firm* — The Morales Law Firm, LLC; Joseph L. Morales

(57) ABSTRACT

The present invention relates to pharmaceutical compositions containing a combination of reduced forms of folate, liver protectors, vitamins, and essential or non-essential amino acids, useful in preventing the adverse effects associated with prolonged use of dihydrofolate reductase inhibitors.

14 Claims, 4 Drawing Sheets

FIGURE 3.

STEP

1. 
| Vitamin B12 and 5-MTHF | Colloidal silicon dioxide |
|---|---|
| Sift through #100 mesh | Sift through #100 mesh |

2. 
| Vitamin B12 and 5-MTHF in Colloidal silicon dioxide |
|---|
| Geometric dilution, mixing 5 min each dilution |

3. 
| Vitamins B2, B6 and premix in the step 2 | Vitamins B2 and B6 |
|---|---|
| Mix for 5 minutes | Sift through #40 mesh and add to step 2 |

4. 
| Milk thistle and premix in the step 3 | Milk thistle and Sodium CMC |
|---|---|
| Mix for 5 minutes | Sift through #30 mesh and and add to step 3 |

5. 
| L-methionine, L-serine and L-Glycine |
|---|
| Sift through #20 mesh and premix for 5 minutes |

6. 
| Premixes in the steps 4 and 5. |
|---|
| Add to the "V" mixer and mix for 10 minutes |

7. 
| Rice floor |
|---|
| Sift through #30 mesh, add to the "V" mixer and mix for 5 minutes |

8. 
| Vegetable magnesium stearate |
|---|
| Sift through #60 mesh, add to the "V" mixer and mix for 3 minutes |

9. 
| Blend in the step 8 and capsules |
|---|
| Capsule filling |

PHARMACEUTICAL COMPOSITION EFFECTIVE IN PREVENTING THE ADVERSE EFFECTS ASSOCIATED WITH THE PROLONGED USE OF DIHYDROFOLATE REDUCTASE INHIBITORS

FIELD OF THE INVENTION

The present invention relates to pharmaceutical compositions containing combinations of folates, liver protectors, vitamins and essential or non-essential amino acids, useful in preventing adverse effects associated with prolonged use of dihydrofolate reductase inhibitors.

BACKGROUND OF THE INVENTION

The dihydrofolate reductase (DHFR) inhibitors are a group of chemical compounds that block the DHFR enzyme, whose main function is to reduce the different forms of folate from the diet to its active form, tetrahydrofolate (THF).

Since the folate in its active form, THF, is used by the cell to produce purines and pyrimidines, which are nitrogenous bases that make up DNA, DHFR has been widely used as a therapeutic target for the treatment of multiple pathological conditions.

Among DHFR inhibitors, methotrexate (MTX) and pemetrexed are the most significant, which are used for, among other applications, in cancer chemotherapy because they are able to prevent the neoplastic cells division.

Microorganisms also need DHFR to grow and multiply, so inhibitors with greater affinity for microbial DHFR are also used in therapy as antibiotic agents; such is the case of trimethoprim (an antibacterial drug) and pyrimethamine (an antiprotozoal drug).

There are treatments for neoplastic diseases such as non-Hodgkin's lymphoma, gestational choriocarcinoma, chorioadenoma, breast cancer, epidermoid cancer, head and neck cancer, T cells cutaneous lymphoma, and lung cancer, in which the prolonged use of DHFR inhibitors in high doses is required. Sustained inhibition of DHFR generates folate deficiencies in its active form, by blocking the body's mechanism to convert folic acid into THF. Due to the high risk of folate deficiency during these types of treatments, medical protocols include folate supplementation in the form of calcium folinate by parenteral route. In this case, the supplementation by parenteral route is feasible because these patients have life-threatening diseases, are hospitalized or go very often to the hospital, and have catheters or venous access devices through which the supplementation can be performed, devices which are usually the same ones used for chemotherapy administration.

On the other hand, there is a group of treatments with DHFR inhibitors that also have a high potential to cause folate deficiencies, for which supplementation with parenteral calcium folinate is not practical because these are outpatients undergoing long-term oral, intramuscular or subcutaneous drug therapy, where venous access is not available. These patients are suffering from rheumatoid arthritis, juvenile rheumatoid arthritis, and psoriasis, which are treated for months, or even years, with low doses of MTX.

In this group of treatments where inhibition of DHFR is also maintained for long periods of time, the conversion of folic acid into THF cannot be carried out properly. That situation, added to the fact that folate supplementation is not included in the treatment protocol, makes folate deficiency in its active form very common in these patients.

The adverse effects caused by DHFR inhibitors are largely due to the same mechanism of action by which they exert their pharmacological effect: decreasing the normal levels of the active form of folate (THF) by inhibiting the DHFR enzyme, which blocks the reduction or activation of folic acid from the diet (FIG. 1).

The adverse effects occurring with prolonged use of low doses of MTX can be classified into three main groups: gastrointestinal adverse effects, mucocutaneous adverse effects and hematological adverse effects.

At gastrointestinal level, folate deficiency may manifest as nausea, anorexia, mild diarrhea, severe ulceration, and bleeding. At mucocutaneous level, the most common manifestation is mouth sores, whereas at hematological level, folate deficiency may decrease the amount of blood cells produced by the bone marrow causing anemia, which in turn manifests as excessive tiredness, paleness, or shortness of breath.

In addition to the adverse effects caused by folate deficiency, at the hepatic level MTX increases transaminases apparently by direct toxicity to the hepatocyte, due to inhibition of synthesis of DNA and RNA in the liver, causing cell deterioration.

For patients treated with MTX, oral folic acid supplementation is not effective because, as mentioned above, folic acid needs the DHFR enzyme to be converted into the active form, THF. When that enzyme is inhibited, the activation step of folic acid by conversion into THF cannot occur, and folate deposits cannot be restored.

Moreover, supplementation of folate alone is not enough to avoid comprehensively the occurrence of adverse effects due to the treatment with MTX because, as mentioned before, the toxic effect on the liver is caused by a direct effect of MTX on the hepatocyte; so, the restoration of deposits of folate by intravenous administration should be accompanied with a protective action on the liver that prevents elevation of transaminases.

Therefore, there is the need, in the state of the art, of means to restore the decreased folate deposits due to MTX treatment with an oral pharmaceutical composition to allow the administration of a form of folate that does not require the mediation of DHFR to become active, which also protects the liver against the action of MTX.

In the state of the art there are some documents including compositions containing folate, such as the International Publication WO 2007/013987, which discloses a composition for improving the methylation process and reducing the likelihood that the individual will develop clinical conditions caused by deficiency in the methylation process. This composition comprises vitamin B6, folic acid, vitamin B12, betaine and silymarin.

The U.S. Pat. No. 7,947,662 discloses a composition for the treatment of diseases such as psoriasis and arthritic and inflammatory conditions, which comprises folic acid, vitamins, botanical extracts and some amino acids. This composition is chemically stable and has high water solubility of folates and/or reduced folates.

The American Publication US 2014/0073598 discloses compositions to be used in patients lacking the ability to convert folic acid into its metabolically active forms, and in the treatment of depression. This composition comprises folate, vitamin B12 and vitamin B6.

The U.S. Pat. No. 8,642,581 discloses the method to increase the levels of S-adenosylmethionine in the human body without the administration of S-adenosylmethionine, by the direct administration of L-methionine, methylcobalamin, 5-methyltetrahydrofolate, betaine, and malic acid with at least one compound selected from the group consisting of folic acid, vitamin B12, magnesium, calcium, and other cofactors.

However, the state of the art does not provide compositions easy to administer that allow the administration of the active form of folate, while protecting the liver against the adverse effects associated with a prolonged treatment with DHFR inhibitors, such as MTX.

SUMMARY OF THE INVENTION

The main object of the present invention is to provide a pharmaceutical composition capable of mitigating the adverse effects caused by prolonged use of DHFR inhibitors, containing a reduced form of folate, a standardized milk thistle extract (*Silybum marianum*), vitamin B complex, essential and non-essential amino acids and pharmaceutically acceptable excipients.

A second object of this invention is to provide a method of preparing the above pharmaceutical composition.

A third object of this invention is a method of treatment to relieve the adverse effects associated with prolonged use of DHFR inhibitors.

A fourth object of this invention is the use of the pharmaceutical composition in patients in need, mainly in patients under long treatment with DHFR inhibitors, such as patients suffering from rheumatoid arthritis, juvenile rheumatoid arthritis, and psoriasis.

DESCRIPTION OF DRAWINGS

The above and other features, aspects, and advantages of the present invention are considered in more detail in relation to the following descriptions of embodiments thereof shown in the accompanying drawings:

FIG. 3. Flow diagram for preparing a pilot batch of a pharmaceutical composition comprising reduced folate. It shows the steps necessary to reach the formulation of interest, including screenings of various components, optimum times of mixtures, premixtures, and capsule filling.

DETAILED DESCRIPTION OF THE INVENTION

Figure 1:
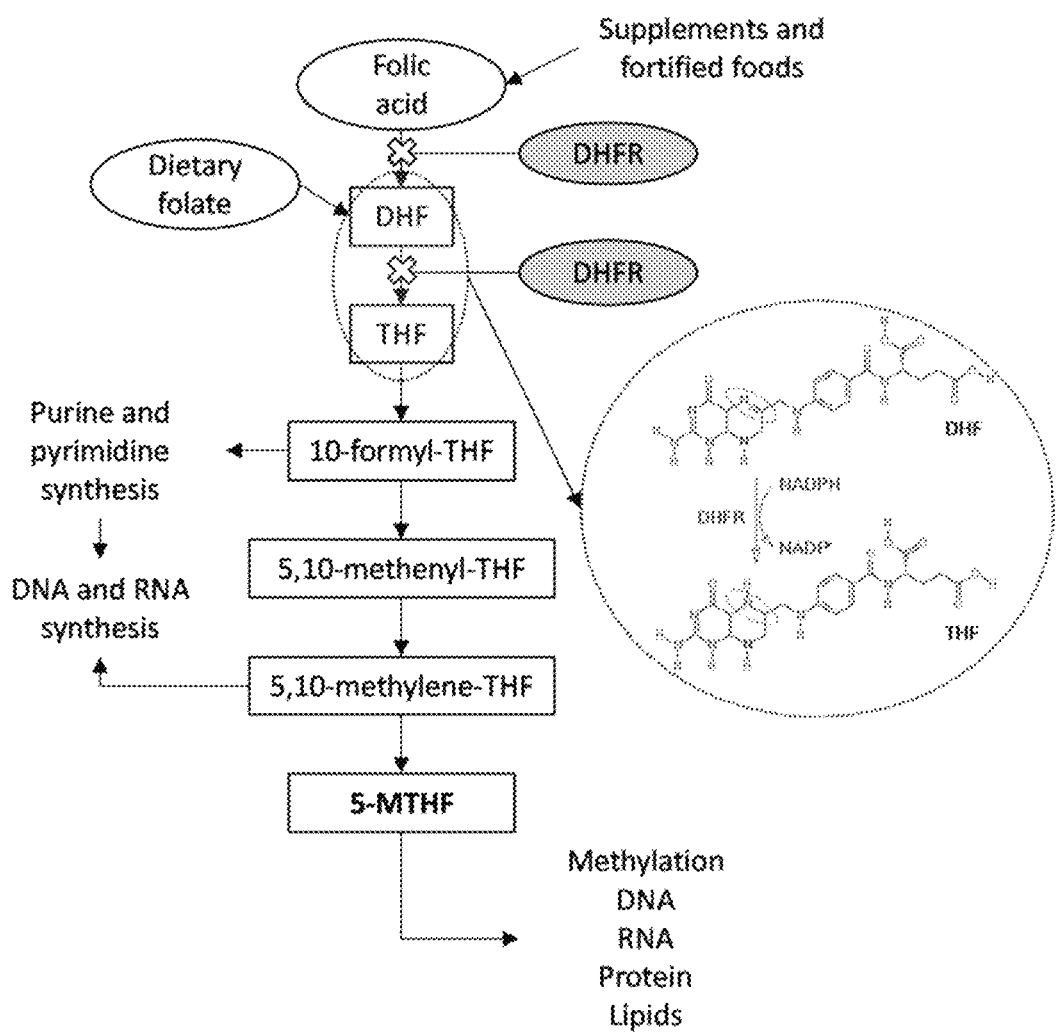
FIG. 1. Activation route of folic acid from the diet. It shows the reduction of folate to THF by the enzyme DHFR, and the role of THF into the biological processes of methylation and synthesis of DNA and RNA.

The invention summarized above and defined by the enumerated claims may be better understood by referring to the following description, which should be read in conjunction with the accompanying drawings. This description of an embodiment, set out below to enable to build and use an implementation of the invention, is not intended to limit the invention, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Prior to the detailed description of the invention, definitions of some terms will follow.

The term "comprising" should be understood as not limiting. For the expected purposes of the present invention, the term "containing" is considered preferred to the term "composed of". If hereinafter a group is defined as comprising a number of embodiments, it is intended to encompass a group consisting of such embodiments preferably. The use of the letter "a" in claim elements does not limit the element to a single component, but includes the use of multiple numbers of the element. The term "selected from the group consisting of" means that one or more of the items of the group may be selected as part of the composition.

In general terms, a "pharmaceutical dosage form" will be understood as a formulation comprising an active ingredient in a specific amount in order to achieve a specific result. A "pharmaceutically acceptable excipient" means an excipient that is acceptable for use in a pharmaceutical formulation for human or animal consumption.

The term "geometric dilution" is a process by which a homogeneous mixture of two or more substances is achieved. When this method is used, the smallest amount of the active ingredient is mixed thoroughly with an equal volume of the diluent. More diluent is added in amounts equal to the volume of the mixture. This process is repeated until all the diluent is incorporated into the mixture. This method, without taking a long time, will create a homogeneous mixture of the drug in the diluent.

The term "dihydrofolate reductase" or "DHFR" refers to the enzyme whose main function is the conversion of dihydrofolate (DHF) into tetrahydrofolate (THF), the active form of folic acid, which can be used, among other processes, in the process of synthesis of purine and pyrimidine bases, which make up DNA and RNA.

The term "methotrexate" or "MTX" is an inhibitory drug of the enzyme dihydrofolate reductase (DHFR), with antagonist properties of folic acid, widely used in the therapy of autoimmune disorders like rheumatoid arthritis, juvenile rheumatoid arthritis, and psoriasis.

The term "pemetrexed" is a DHFR inhibitory drug, widely used in the treatment of different types of tumors.

The term "reduced form of folate" is the active form of folate, which does not require the mediation of dihydrofolate reductase (DHFR) to perform its function in the synthesis of DNA and RNA.

The term "5-methyltetrahydrofolate" or "5-MTHF" is one of the reduced forms of the folate ion.

The term "standardized extract" is an extract that ensures the same amount of active ingredients, irrespective of the batch and date of manufacture.

The term "comprehensive manner" refers to the treatment of the different causes of adverse effects as a whole, rather than treating them separately.

The term "essential amino acid" refers to a family of amino acids that cannot be synthesized by the human body and, thus, must enter the human body through ingestion, injection, or other similar means. The term "non-essential amino acid" refers to the type of amino acid that can be synthesized within the human body when the appropriate compounds are present.

The present invention discloses a novel pharmaceutical composition for use in preventing the adverse effects resulting from prolonged administration of DHFR inhibitors, such as MTX, pemetrexed, trimethoprim and pyrimethamine, which, according to medical criteria, are highly likely to cause folate deficiency.

MTX in high doses decreases the supply of folate in its active form and inhibits the synthesis of purines and pyrimidines, becoming it useful in the treatment of malignant tumors. On the other hand, at low doses (<20 mg/week), MTX is commonly used as the standard systemic therapy for severe psoriasis, rheumatoid arthritis, and juvenile rheumatoid arthritis.

Deficiency of folate in its active form is the main mechanism by which patients treated with MTX develop mucocutaneous, gastrointestinal and hematologic adverse effects; therefore, the administration of folate supplements in the form or folic or folinic acid, is often used concomitantly with MTX to minimize adverse effects.

In addition to folate deficiency, MTX can cause different histological changes in the liver, including steatosis, hypertrophy of stellate cells, anisonucleosis (nuclei of different sizes) and liver fibrosis. Apparently, these effects are due to direct liver toxicity caused by MTX on the hepatocyte.

During the treatment of malignant tumors when high doses of DHFR inhibitors are used, injections of calcium folinate are often included in the treatment protocol; however, when low doses are used, the administration of folate supplements is not included in the treatment protocol, although it could be justified, especially in patients suffering from psoriasis, rheumatoid arthritis, and juvenile rheumatoid arthritis under treatment with MTX.

Following are some of the adverse effects caused by prolonged treatment with low-dose MTX:

Gastrointestinal effects, such as gastrointestinal intolerance.

Mucocutaneous effects, such as stomatitis or mouth sores.

Hematological effects, such as bone marrow toxicity (megaloblastic anemia)

Hepatic effects, such as abnormal liver function and increase in plasma liver transaminase levels, indicating cell damage.

Oral supplementation with folic acid does not solve efficiently the problem of adverse effects associated with long-term use of MTX, since folic acid itself does not possess biological activity; on the contrary, it requires the DHFR enzyme to turn into its active form (THF), and it is this enzyme which is inhibited during treatment with MTX.

Because of the above, folic acid is not an effective alternative for administering the active form of folate in patients treated with MTX. For optimum results in these cases, the administration of a reduced form of folate, active by itself, and not dependent on DHFR to exert its action is required. Moreover, the comprehensive treatment of adverse effects associated with long-term use of MTX requires, besides an effective folate supplementation, an agent to reduce the direct toxicity that MTX exerts on the hepatocyte. The present invention is a novel pharmaceutical composition capable of preventing, in a comprehensive manner, the adverse effects resulting from long-term treatment with DHFR inhibitors, as in the case of treatment with drugs selected from the group consisting of MTX, Pemetrexed, Trimethoprim or Pirimietamina, especially in patients with rheumatoid arthritis, juvenile rheumatoid arthritis, or psoriasis under treatment with MTX.

Surprisingly, it has been found that the pharmaceutical composition of the present invention, comprising a reduced form of folate, a standardized milk thistle extract (*Silybum marianum*), vitamins belonging to the B complex, essential and non-essential amino acids and pharmaceutically acceptable excipients, given by oral route, significantly mitigates the adverse effects of MTX treatment in patients suffering from rheumatoid arthritis, juvenile rheumatoid arthritis, or psoriasis.

In a preferred embodiment, the pharmaceutical composition of the present invention comprises a folate selected from the group consisting of 5-methyltetrahydrofolate, folinic acid, calcium folinate and folic acid. Preferably, it comprises a folate selected from a reduced form of folate, such as 5-methyltetrahydrofolate (5-MTHF), folinic acid and calcium folinate, and more preferably, it comprises 5-MTHF, which is present in an amount that can vary from 200 µg to 5 mg, and more preferably from 800 µg to 2 mg.

In a preferred embodiment, the pharmaceutical composition of the present invention comprises vitamins belonging to B complex, more preferably vitamin B12, vitamin B6 and vitamin B2. Vitamin B12 may be selected from methylcobalamin, hydroxycobalamin and cinaocobalamina. Vitamin B6 may be selected from pyridoxine hydrochloride, pyridoxine, pyridoxal 5'-phosphate and pyridoxamine. Vitamin B2 is riboflavin.

More preferably, the vitamin B12 selected for the present invention is methylcobalamin, which is present in an amount which can vary between 6 µg and 1,000 µg, and more preferably between 25 µg and 100 µg.

More preferably, the vitamin B6 selected for the present invention is pyridoxine hydrochloride, which is present in an amount which can vary between 2 mg to 100 mg, and more preferably between 5 mg and 50 mg. The vitamin B2 selected for the present invention is riboflavin, which is present in an amount which can vary between 1.7 mg to 100 mg, and more preferably between 2.5 mg and 50 mg.

In a preferred embodiment, the pharmaceutical composition of the present invention comprises an extract of milk thistle, (*Silybum marianum*), which is standardized to 80% silymarin and present in an amount which can vary between 40 mg to 400 mg, and more preferably between 75 mg and 200 mg. In a preferred embodiment, the pharmaceutical composition of the present invention comprises essential and non-essential amino acids selected from the group consisting of L-methionine, DL-methionine, S-adenosyl-L-methionine, S-adenosyl-L-methionine tosylate disulfate; L-serine, DL-serine, phosphatidyl serine; and L-glycine, DL-glycine, trimethyl glycine.

More preferably, the essential amino acid selected for the present invention is L-methionine, which is present in an amount that can vary from 25 mg to 400 mg, and more preferably between 50 mg and 250 mg. The non-essential amino acids selected are L-serine, which is present in an amount that can vary from 25 mg to 400 mg, and more preferably between 50 mg and 250 mg, and L-glycine, which is present in an amount that can vary between 25 mg to 400 mg, and more preferably between 50 mg and 250 mg.

In addition to the active components mentioned above, the pharmaceutical composition of the invention can be prepared with a wide range of pharmaceutically acceptable excipients and carriers, which are known in the state of the art, such as binders, disintegrants, lubricants, glidants, diluents, solvents, among others. Likewise, the preferred dosage form of the invention is selected from tablet, hard capsule, soft capsule and powder, being hard capsule the most preferred.

In one exemplary embodiment of the present invention, a pharmaceutical composition contains, but is not limited to, the following:

TABLE 1

Active components and amounts per capsule

| Active Ingredients | Amount per Capsule |
| --- | --- |
| Folate (as 5-methytetrahydrofolate) | 200.0 µg-5.0 mg |
| Vitamin B12 (as methylcobalamin) | 6.0 µg-1,000.0 µg |
| Vitamin B6 (as pyridoxine hydrochloride) | 2.0 mg-100.0 mg |
| Vitamin B2 (as riboflavin) | 1.7 mg-100.0 mg |
| Milk thistle extract (*Silybum marianum*) (standardized to 80% silynnarin) | 40.0 mg-400.0 mg |
| L-methionine | 25.0 mg-400.0 mg |
| L-serine | 25.0 mg-400.0 mg |
| L-glycine | 25.0 mg-400.0 mg |

The following examples illustrates the preferred embodiments and are not limiting the scope of the present invention:

Example 1—Solid Composition for 2,000 Capsules

A sample of 2,000 capsules, using the formulation described below, was prepared.

TABLE 2

Sample of 2,000 capsules using the preferred composition

| Active Ingredient | Amount per Capsule | Amount per 2,000 Capsules |
| --- | --- | --- |
| Folate (as 5-methyltetrahydrofolate) | 1,000.0 µg | 2.0 g |
| Vitamin B12 (as methylcobalamin) | 50.0 µg | 0.1 g |
| Vitamin B6 (as pyridoxine hydrochloride) | 10.0 mg | 20.0 g |
| Vitamin B2 (as riboflavin) | 5.0 mg | 10.0 g |
| Milk thistle extract (*Silybum marianum*) (standardized to 80% silymarin) | 150.0 mg | 300.0 g |
| L-methionine | 50.0 mg | 100.0 g |
| L-serine | 100.0 mg | 200.0 g |
| L-glycine | 100.0 mg | 200.0 g |

Excipients for 2,000 capsules: Microcrystalline cellulose, 455.9 g; Sodium croscarmellose, 28.0 g; Colloidal silicon dioxide, 70.0 g; Vegetable magnesium stearate, 14.0 g. The capsule was "#00" standard.

Figure 2:
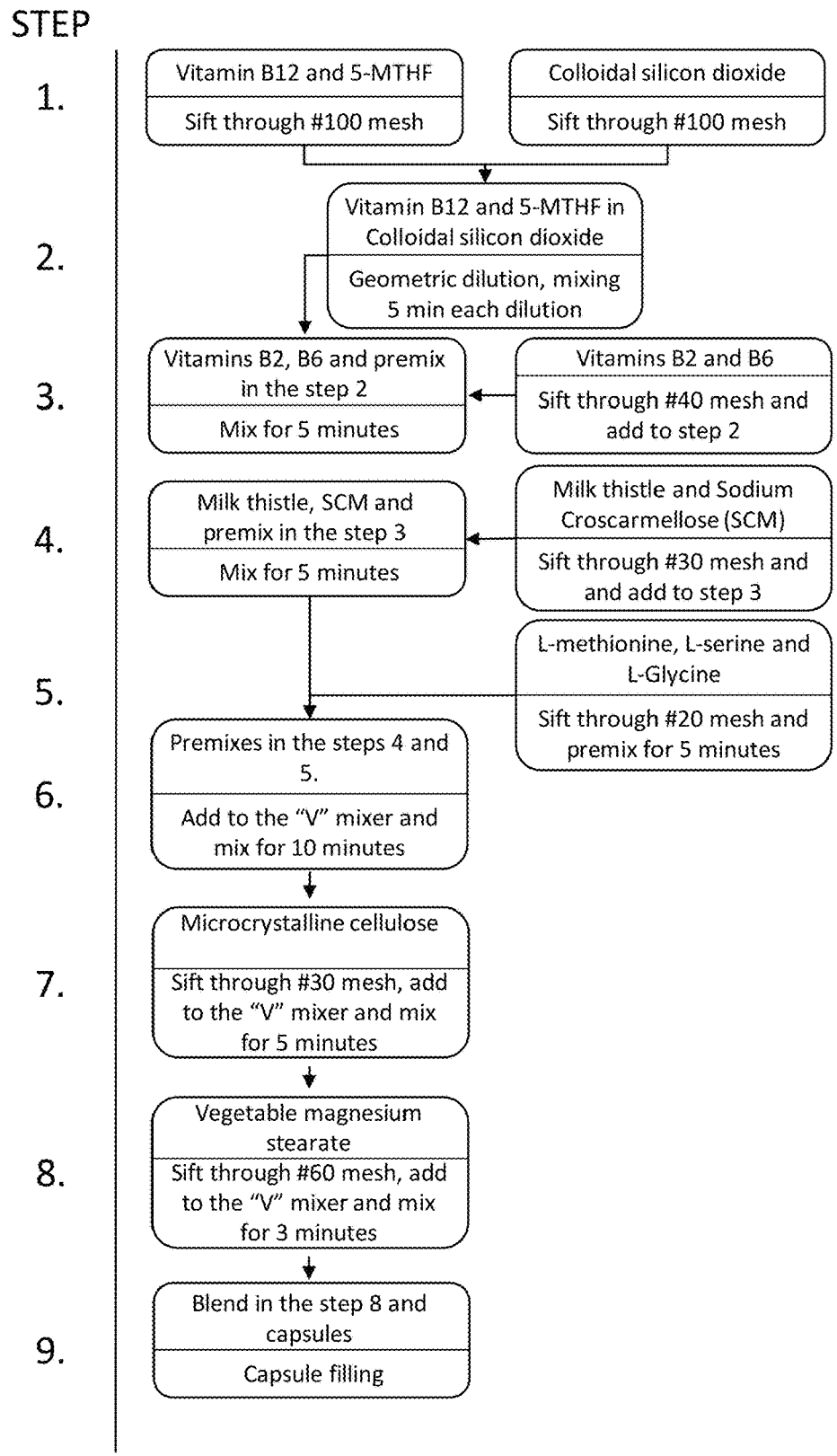
FIG. 2. Flow diagram for preparing a sample of a pharmaceutical composition comprising reduced folate. It shows the steps necessary to reach the formulation of interest, including screenings of various components, optimum times of mixtures, premixtures and capsule filling.

The preferred composition described in Table 2 was prepared by the following method, as shown in FIG. 2:

1. Sift 5-MTHF, vitamin B12 and colloidal silicon dioxide through a mesh #100.
2. Perform a geometric dilution of folate and vitamin B12 in colloidal silicon dioxide and mix for at least 5 minutes after each dilution.
3. Sift vitamins B6 and B2 through a mesh #40, add them to the premix obtained in step 2 and mix for at least 5 minutes.
4. Sift milk thistle extract and sodium croscarmellose through a mesh #30, add them to the preparation of step 3 and mix for at least 5 minutes.
5. Sift the amino acids L-methionine, L-serine and L-glycine through mesh #20 and premix them for at least 5 minutes;
6. Place the premixes obtained in steps 4 and 5 in a "V" mixer and mix for at least 10 minutes.
7. Sift microcrystalline cellulose through a mesh #30, add it to the "V" mixer and mix for at least 5 minutes.
8. Add vegetable magnesium stearate, previously sieved through a mesh #60, to the "V" mixer and mix for no more than 3 minutes.
9. Fill vegetarian capsules "#00" to reach an average weight of 700 mg per capsule.

Example 2—Solid Composition for a Pilot Batch of 20,000 Capsules

Three independent pilot batches of 20,000 capsules, each using the formulation described below, were prepared:

TABLE 3

Sample of 20,000 capsules using the preferred composition

| Active Ingredient | Amount per Capsule | Amount per 20,000 Capsules |
| --- | --- | --- |
| Folate (as 5-methyltetrahydrofolate) | 1,000.0 µg | 20.0 g |
| Vitamin B12 (as methylcobalamin) | 50.0 µg | 1.0 g |
| Vitamin B6 (as pyridoxine hydrochloride) | 10.0 mg | 200.0 g |
| Vitamin B2 (as riboflavin) | 5.0 mg | 100.0 g |
| Milk thistle (*Silybum marianum*) extract (standardized to 80% silymarin) | 150.0 mg | 3,000.0 g |
| L-methionine | 50.0 mg | 1,000.0 g |
| L-serine | 100.0 mg | 2,000.0 g |
| L-glycine | 100.0 mg | 2,000.0 g |

Excipients for 20,000 capsules: Rice flour, 483.9 g; Colloidal silicon dioxide, 70.0 g; Vegetable magnesium stearate, 14.0 g. The capsule was "#00" standard.

The preferred composition Described in Table 3 was prepared by the following method, as shown in FIG. 3:

1. Sift 5-MTHF, vitamin B12 and colloidal silicon dioxide through mesh #100.
2. Perform a geometric dilution of folate and vitamin B12 in colloidal silicon dioxide and mix for at least 5 minutes after each dilution.
3. Sift vitamins B6 and B2 through mesh #40, add them to the premix obtained in step 1 and mix for at least 5 minutes.
4. Sift milk thistle extract through mesh #30, add them to the preparation of step 3 and mix for at least 5 minutes.
5. Sift the amino acids L-methionine, L-serine and L-glycine through mesh #20 and premix them for at least 5 minutes;
6. Place the premixes obtained in steps 4 and 5 in a "V" mixer and mix them for at least 10 minutes.
7. Sift rice flour through mesh #30, add it to the "V" mixer and mix for at least 5 minutes.
8. Add vegetable magnesium stearate, previously sieved through a mesh #60, to the "V" mixer and mix for no more than 3 minutes.
9. Fill hard gelatin capsules "#00" to reach an average weight of 700 mg per Capsule.

Example 3—Stability of the Composition

Using three pilot batches, manufactured as described in Example 2, stability studies under both conditions, accelerated and long term, were carried out. The conditions of the studies were as follows:

Accelerated storage conditions: 40° C.±2° C./75%±5% of relative humidity.

Long term storage conditions: 30° C.±2° C./65%±5% of relative humidity.

Duration of the accelerated study: 6 months

Duration of the natural study: 36 months

Number of pilot batches used in the studies: 3

Packaging material: 100 mL white HDPE bottle with ribbed 38 mm CRC (child resistant cap) and heat sealed, plus cotton, silica as desiccant and folding carton.

The physical parameters evaluated in both studies were the following: physical description, moisture content, average weight, weight variation, disintegration time.

Chemical parameters evaluated in both studies were the following: assay of folate (as 5-MTHF), assay of milk thistle, dissolution of folate (as 5-MTHF), dissolution of vitamin B2 (as riboflavin), and dissolution of milk thistle. Microbiological parameters evaluated in in both studies were the following: total aerobic microbial count (TAMC), total combined yeasts and molds count (TYMC), verification of the absence of *E. coli, Salmonella, S. aureus*, and *Pseudomonas* spp.

The studies were carried out in accordance with the ICH Guidance Q1A (R2) and the Pharmacopeia of the United States in its version 38, chapters <2091>, <2040>, Dietary supplements—Vitamins and Dietary Supplements—Milk Thistle extract.

The results from both studies successfully met the acceptance criteria defined in both the Pharmacopoeia of the United States of America and the ICH Guidance Q1A (R2).

Example 4—Clinical Trial: Reduction in the Development of Hepatic Dysfunction (as Measured by Elevated Serum Transaminase Levels) with Methyltetrahydrofolate and Silymarin in Patients Treated with Low Doses of MTX The following is a non-limiting example of a clinical trial evaluating the use of the preparation of the present invention in preventing the adverse effects associated with prolonged use of low-dose methotrexate, in patients suffering from rheumatoid arthritis, juvenile rheumatoid arthritis, or psoriasis in comparison to the use of the standard preparation of folic acid.

1. Hypothesis: The preparation described in the example 2 taken once a day for 5 days a week for five months in chronic users of MTX for severe psoriasis, rheumatoid arthritis or juvenile rheumatoid arthritis, with elevation of transaminases two fold over normal values, is better to reduce the hepatotoxic effect of MTX than folic acid alone.
2. Objective: To assess the benefits of the preparation in the example 2 in reducing the hepatotoxic side effects caused by MTX.
3. Study population:
    3.1 Inclusion criteria: Men or women older than 18 years, users of MTX during 1 year or more, with serum transaminase levels two fold over normal levels, and willing to sign the informed consent.
    3.2 Exclusion criteria: Subjects that discontinued the use of the supplement for 4 or more days during the assay; pregnant or lactating women; and people with clinical conditions other than those requiring chronic use of MTX.
    3.3. Population: 30 people divided in two groups of 15 each one.
    3.4. Assignment of subjects: The assignment of subjects will be made in two comparable groups of 15 each one.
4. Supplement to be dispensed: The investigational composition described in the example 2 and the comparative composition containing 1 mg of folic acid will be given once a day for 5 days a week for 5 months, with breakfast. The compositions should not be given the same day patients receive MTX or the next day, according to the posology schedule described in the Table 4.
5. Type of study: This is an experimental, longitudinal, prospective, parallel, double-blind, and randomized clinical assay comparing two MTX chronic user (one year or more) groups.
6. Main outcome: Reduction in the level of hepatic transaminases.
7. Secondary outcome:
    7.1 Reduction in the incidence of gastrointestinal side effects, such as nausea, vomiting or abdominal pain.
    7.2 Reduction in the incidence of stomatitis, mouth sores, and whilst.

Treatment Method

The pharmaceutical composition of the present invention is appropriate in preventing the adverse effects associated with the treatment of patients suffering from psoriasis, rheumatoid arthritis, or juvenile rheumatoid arthritis with MTX for long periods of time. Currently, in clinical practice treatment with MTX is initiated with one of the two dosing schedules listed below:

1. A single weekly dose of 7.5 mg of MTX given orally, subcutaneously or intramuscularly.
2. A total weekly dose of 7.5 mg of MTX given orally, divided in three doses of 2.5 mg, separated by 12 hours.

Subsequently, the dose may be increased according to the therapeutic response and the adverse effect profile, but it should not exceed a total weekly dose of 30 mg.

Figure 4:
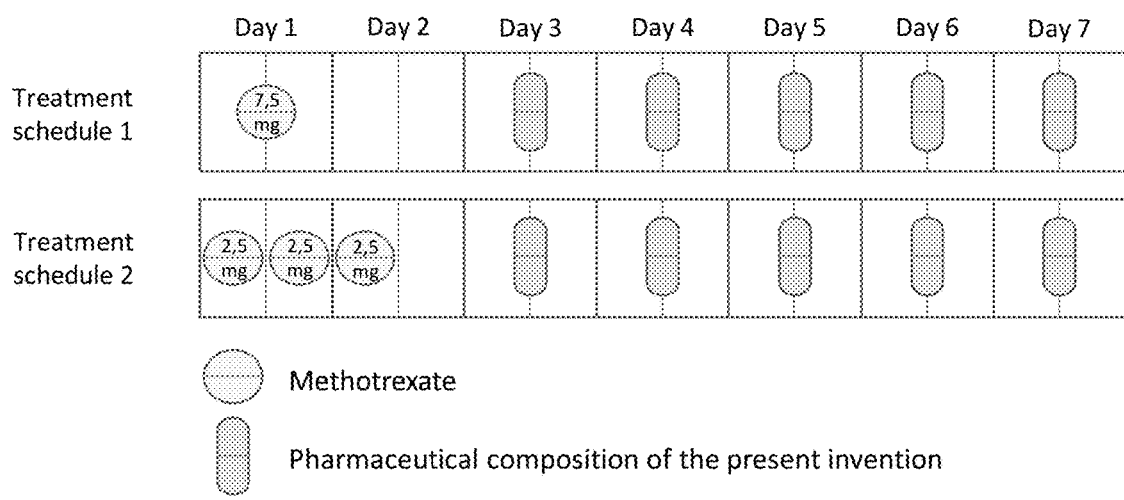
FIG. 4. A schematic representation of the method of treatment. It shows two dosing schedules for administering MTX and the pharmaceutical composition of the present invention.

According to the MTX posology, the oral administration of the pharmaceutical composition of the invention provides better results when taken as follows:

1. Patients starting MTX as a single weekly dose of 7.5 mg, regardless of the route of administration, should wait at least 48 hours after the administration of MTX before taking the pharmaceutical composition of the invention 1 (one) once a day with a meal for 5 consecutive days (Table 4).
2. Patients starting MTX divided into 3 doses of 2.5 mg a week, separated by 12 hours, should wait at least 30 hours after taking the last dose of 2.5 mg of MTX before taking the pharmaceutical composition of the invention, once a day with a meal for 5 consecutive days (FIG. 4)

According to what is described in Example 4, the administration of the pharmaceutical composition of the present invention, as described above, ensures non-interference of folate supplementation with the therapeutic response to MTX and, in turn, ensures optimum results in terms of the reduction in the frequency of adverse effects associated with prolonged use of MTX.

In one preferred embodiment, a method of treatment to prevent adverse effects associated with the long term use of dihydrofolate reductase inhibitors, comprises a) administering the composition of claim 1 to a patient, wherein a first dose of the composition of claim 1 is administered at least 48 hours after the administration of a single dose course of methotrexate; or b) administering the composition of claim 1 to a patient, wherein a first dose of the composition is administered at least 30 hours after the administration of a third dose of a three dose course of methotrexate. Preferably, five doses of the composition are administered to the patient. In a preferred embodiment of the method, the composition is administered orally. In one preferred embodiment of the method the single dose of methotrexate or the three dose course of methothrexate are part of a weekly regiment.

What is claimed is:

1. A tablet or capsule, consisting essentially of:
   a. a reduced form of folate selected from the group consisting of 5-methyltetrahydrofolate, folinic acid, and pharmaceutically acceptable salts thereof;
   b. milk thistle standardized extract;
   c. at least one B complex vitamin; and
   d. at least one amino acid selected from the group consisting of L-methionine, DL-methionine, S-adenosyl-L-methionine, S-adenosyl-L-methionine tosylate disulfate, L-serine, DL-serine, phosphatidyl serine, and L-glycine, DL-glycine, timethyl glycine.

2. The tablet or capsule of claim 1, wherein the reduced form of folate is 5-methyltetrahydrofolate.

3. The tablet or capsule of claim 1, wherein the milk thistle extract is a standardized extract to 80% silymarin.

4. The tablet or capsule of claim 1, wherein the B complex vitamin is selected from the group consisting of vitamin B12, vitamin B6, and vitamin B2.

5. The tablet or capsule of claim 4, wherein the vitamin B12 is selected from the group consisting of methylcobalamin, cyanocobalamin, and hydroxycobalamin; the vitamin B6 is selected from the group consisting of pyridoxine, pyridoxal 5'phosphate, pyridoxamine, and pyridoxine hydrochloride; and the vitamin B2 is riboflavin.

6. The tablet or capsule of claim 4, wherein the vitamin B12 is methylcobalamin; the vitamin B6 is pyridoxine hydrochloride; and the vitamin B2 is riboflavin.

7. A tablet or capsule, consisting essentially of:
   a. Folate, in an amount between 200.0 µg and 5.0 mg;
   b. Milk thistle extract, in an amount between 40.0 mg and 400.0 mg;
   c. Vitamin B12 as methylcobalamin, in an amount between 6.0 µg and 1,000.0 µg;
   d. Vitamin B6 as pyridoxine hydrochloride, in an amount between 2.0 mg and 100.0 mg;
   e. Vitamin B2 as riboflavin, in an amount between 1.7 mg and 100.0 mg;
   f. L-Methionine, in an amount between 25.0 mg and 400.0 mg;
   g. L-Serine, in an amount between 25.0 mg and 400.0 mg; and
   h. L-Glycine, in an amount between 25.0 mg and 400.0 mg.

8. A tablet or capsule, consisting essentially of:
   a. Folate, in an amount of 800.0 µg and 2.0 mg;
   b. Milk thistle extract, in an amount between 75.0 mg and 200.0 mg;
   c. Vitamin B12 as methylcobalamin, in an amount between 25.0 µg and 100.0 µg;
   d. Vitamin B6 as pyridoxine hydrochloride, in an amount between 5.0 mg and 50.0 mg;
   e. Vitamin B2 as riboflavin, in an amount between 2.5 mg and 50.0 mg;
   f. L-Methionine, in an amount between 50.0 mg and 250.0 mg;
   g. L-Serine, in an amount between 50.0 mg and 250.0 mg; and
   h. L-Glycine, in an amount between 50.0 mg and 250.0 mg.

9. A tablet or capsule, consisting essentially of:
   a. at least one of 5-methyltetrahydrofolate, folinic acid, and pharmaceutically acceptable salts thereof;
   b. milk thistle standardized extract;
   c. at least one of vitamins B2, B6, and B12; and
   d. at least one of L-methionine, L-serine, and L-glycine.

10. A method of treatment to prevent adverse effects associated with the long term use of dihydrofolate reductase inhibitors, comprising:
    a) administering the composition of claim 1 to a patient, wherein a first dose of the composition of claim 1 is administered at least 48 hours after the administration of a single dose course of methotrexate; or
    b) administering the composition of claim 1 to a patient, wherein a first dose of the composition of claim 1 is administered at least 30 hours after the administration of a third dose of a three dose course of methotrexate.

11. The method of claim 10, wherein five doses of the composition of claim 1 are administered to the patient.

12. The method of claim 10, wherein the composition of claim 1 is administered orally.

13. The method of claim 10, wherein the single dose of methotrexate or the three dose course of methothrexate are part of a weekly regiment.

14. A method of using the composition according to claim 1, comprising:
    administering a pharmaceutical dosage form of the composition of claim 1 orally to a patient subject to treatment with dihydrofolate reductase inhibitors selected from the group consisting of Methotrexate, Pemetrexed, Trimethoprim and Pyrimethamine.

* * * * *